United States Patent
Bailey et al.

(10) Patent No.: US 11,681,266 B2
(45) Date of Patent: Jun. 20, 2023

(54) DATA CENTER MANAGEMENT SYSTEM THAT CONTROLS ENVIRONMENTAL CONDITIONS TO FACILITATE OPERATING STATE CHANGES OF INDIVIDUAL EQUIPMENT

(71) Applicant: DELL PRODUCTS, L.P., Round Rock, TX (US)

(72) Inventors: Mark M. Bailey, Round Rock, TX (US); Tyler B. Duncan, Austin, TX (US)

(73) Assignee: Dell Products, L.P., Round Rock, TX (US)

( * ) Notice: Subject to any disclaimer, the term of this patent is extended or adjusted under 35 U.S.C. 154(b) by 631 days.

(21) Appl. No.: 16/738,782

(22) Filed: Jan. 9, 2020

(65) Prior Publication Data

US 2021/0216057 A1 Jul. 15, 2021

(51) Int. Cl.
| | |
|---|---|
| G05B 19/05 | (2006.01) |
| G01K 3/00 | (2006.01) |
| G01K 13/00 | (2021.01) |
| G01N 33/00 | (2006.01) |
| G06F 11/30 | (2006.01) |

(52) U.S. Cl.
CPC .......... *G05B 19/058* (2013.01); *G01K 3/005* (2013.01); *G01K 13/00* (2013.01); *G01N 33/0027* (2013.01); *G06F 11/3006* (2013.01); *G06F 11/3058* (2013.01); *G05B 2219/14043* (2013.01)

(58) Field of Classification Search
CPC ........ G05B 19/058; G05B 2219/14043; G01K 3/005; G01K 3/00; G01N 33/0027; G06F 11/3006; G06F 11/3058
USPC ........................................................ 700/282
See application file for complete search history.

(56) References Cited

U.S. PATENT DOCUMENTS

| | | | |
|---|---|---|---|
| 9,679,087 B2 | 6/2017 | Hamann et al. | |
| 2009/0235097 A1 | 9/2009 | Hamilton et al. | |
| 2015/0088314 A1 | 3/2015 | Dasari et al. | |
| 2016/0198593 A1* | 7/2016 | Schmitt | H05K 7/20745 361/679.49 |
| 2018/0164841 A1 | 6/2018 | Lovicott et al. | |
| 2021/0204448 A1* | 7/2021 | Wiederhold | H05K 7/20745 |

\* cited by examiner

*Primary Examiner* — Michael P Nghiem
(74) *Attorney, Agent, or Firm* — Isidore PLLC

(57) ABSTRACT

A management system controls environmental conditions to facilitate operating state changes of individual information technology (IT) equipment within a data center. A management controller accesses a specification data structure containing environmental conditions specified to enable each one of the IT components to function in operational operating state(s). The management controller determines a temperature range specified in the specification data structure for a first IT component that is scheduled to transition into a first operational state. The management controller adjusts a temperature set point of supply air provided by the data center to the first IT component to be within the temperature range. In response to determining that the interior air temperature is within the temperature range, the management controller triggers activation of the first IT component into the first operating state.

16 Claims, 11 Drawing Sheets

DATA CENTER MANAGEMENT SYSTEM THAT CONTROLS ENVIRONMENTAL CONDITIONS TO FACILITATE OPERATING STATE CHANGES OF INDIVIDUAL EQUIPMENT

BACKGROUND

1. Technical Field

The present disclosure generally relates to a data center with a management system, and in particular to a management system that controls temperature and humidity within the data center.

2. Description of the Related Art

As the value and use of information continue to increase, individuals and businesses seek additional ways to process and store information. One option available to users is information handling systems. An information handling system generally processes, compiles, stores, and/or communicates information or data for business, personal, or other purposes, thereby allowing users to take advantage of the value of the information. Because technology and information handling needs and requirements vary between different users or applications, information handling systems may also vary regarding what information is handled, how the information is handled, how much information is processed, stored, or communicated, and how quickly and efficiently the information may be processed, stored, or communicated. The variations in information handling systems allow for information handling systems to be general or configured for a specific user or specific use such as financial transaction processing, airline reservations, enterprise data storage, or global communications. In addition, information handling systems may include a variety of hardware and software components that may be configured to process, store, and communicate information and may include one or more computer systems, data storage systems, and networking systems.

Information technology (IT) equipment, such as information handling systems housed in an IT space of a data center, often has environmental specifications that are preferred for non-operation, startup and operation states. The environmental specifications provide for reliable operation of the IT equipment and protect service life of the IT equipment. The non-operational specifications are typically the least strict. The startup conditions can be equal to or stricter than the normal operating environmental specifications. The specified temperature ranges within the environmental specifications prevent condensation or thermal expansion/contraction issues from occurring in internal components of the IT equipment when the IT equipment is transitioning from the non-operational state to the normal operational state. During startup of an environmental subsystem of a data center, temperature within the IT space can be outside of a specified temperature range for operation of the IT equipment. IT equipment can be damaged if allowed to start prior to the environmental subsystem bringing the interior air temperature within the specified temperature range. During continued operation of the data center, additional IT equipment that was unnecessary during an initial startup and operational phase of the data center can be brought into operational state. For example, new IT equipment can be introduced to the data center during an upgrade or maintenance procedure. A current temperature range of the IT space of the data center during ongoing operation can be within a temperature range specified for an operational state (e.g., start or operation) for the initial IT equipment; however, the current temperature range of the IT space can be outside of the range of temperatures specified for additional IT equipment that is to be activated.

BRIEF SUMMARY

Disclosed are a data center, and management system of a data center, and a method for protecting internal components of a data center from being exposed to a temperature range that is not specified for a current operational state of the internal components.

According to one embodiment, a method includes processes for controlling interior environmental conditions to facilitate operating state changes of individual information technology (IT) equipment in a data center. The method includes monitoring sensor(s) that detect an interior air temperature value of a data center containing information technology (IT) components. The method includes accessing a specification data structure containing environmental conditions specified to enable each one of the IT components to function in one or more operational state. The method includes determining, by a controller, a first temperature range specified in the specification data structure for a first IT component of the IT components that is scheduled to transition into a first operational state. The method includes adjusting a temperature set point of supply air provided by the data center to the first IT component to be within the first temperature range. The method includes determining whether the temperature of the supply air provided to the first IT component is at/within the first temperature range. In response to determining that the interior air temperature is within the first temperature range, the method includes triggering the first IT component to begin operating in the first operational state.

According to a next embodiment, a management system is provided that controls interior environmental conditions to facilitate operating state changes of individual IT equipment in a data center. The management system includes an environmental subsystem that provide supply air to moderate or cool a temperature of IT components within the data center. The management system includes sensor(s) that detect an interior temperature value of the data center. The management system includes a memory containing a cooling mode and equipment operating state (CM/EOS) application and a specification data structure containing environmental conditions specified to enable each one of the IT components to function in one or more operational states. The management system includes a controller that is communicatively coupled to the environmental subsystem, the sensor(s), and the memory. The controller executes the CM/EOS application to enable the management system to monitor and receive current values from the temperature sensor(s). The controller determines a first temperature range specified for a first IT component that is scheduled to transition into the first operational state. The CM/EOS application enables the management system to adjust a temperature set point of supply air provided by the environmental subsystem to the first IT component to be within the first temperature range. The management system determines whether the temperature of the supply air provided to the first IT component is at/within the first temperature range. The CM/EOS application enables the management system to trigger the activation/entry of the first IT component into the first operational state, in response to determining that the interior air temperature is within the first temperature range.

According to another embodiment, a data center controls interior environmental conditions to facilitate operating state changes of individual IT equipment. The data center includes heat-generating IT components positioned in an enclosing structure and a management system. The management system includes an environmental subsystem that provide supply air to moderate or cool a temperature of the IT components. The management system includes sensor(s) that detect an interior temperature value of the data center. The management system includes a memory containing a CM/EOS application and a specification data structure containing environmental conditions specified to enable each one of the IT components to function in one or more operational states. The management system includes a controller that is communicatively coupled to the environmental subsystem, the sensor(s), and the memory. The controller executes the CM/EOS application to enable the management system to monitor the sensor(s) that detect the interior air temperature value and access the specification data structure. The controller determines a first temperature range specified in the specification data structure for the first IT component that is scheduled to transition into the first operational state. The CM/EOS application enables the management system to adjust a temperature set point of supply air provided by the environmental subsystem to the first IT component to be within the first temperature range. The CM/EOS application enables the management system to determine whether the temperature of the supply air provided to the first IT component is at/within the first temperature range. The CM/EOS application enables the management system, in response to determining that the interior air temperature is within the first temperature range, to activate the first IT component to the first operational state.

BRIEF DESCRIPTION OF THE DRAWINGS

The description of the illustrative embodiments can be read in conjunction with the accompanying figures. It will be appreciated that for simplicity and clarity of illustration, elements illustrated in the figures have not necessarily been drawn to scale. For example, the dimensions of some of the elements are exaggerated relative to other elements. Embodiments incorporating teachings of the present disclosure are shown and described with respect to the figures presented herein, in which.

DETAILED DESCRIPTION

Figure 1:
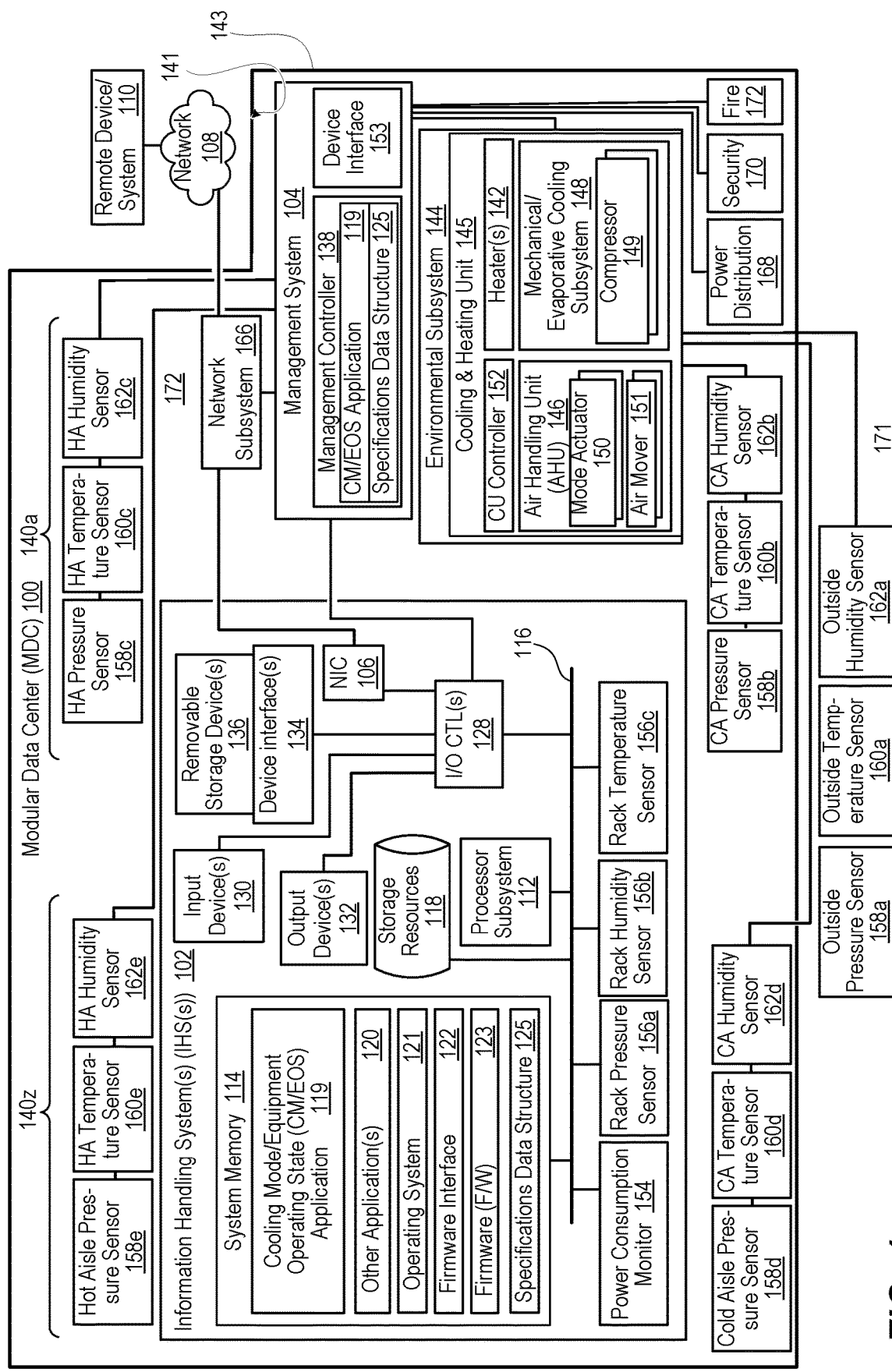
FIG. 1 depicts a simplified functional block diagram of a modular data center (MDC), according to one or more embodiments.

The illustrative embodiments provide a data center, a management system of a data center, and a method for controlling interior environmental conditions to facilitate operating state changes of individual information technology (IT) equipment in a data center. The management system adjusts environmental conditions within the data center to comply with temperature, humidity, and temperate change rates specified for operating states of particular IT components of the data center. The temperature change rate is a maximum amount of change in temperature over a particular unit of time. The management system prevents an operating state change of each IT component until the specified environmental conditions are met, preventing damage or reduction in service life of each IT component. Operating states can include non-operational (inactive/OFF) state, standby/sleep state, start-up state (first operating state), and operational state (second operating state).

A notional example of specified environmental conditions for a particular IT component is provided in TABLE 1:

TABLE 1

| Maximum temperature gradient (applies to both operation and non-operation) | (a) General: 20° C. in an hour and 5° C. in 15 minutes; (b) HDD: 5° C. in 15 minutes, with no cold start-ups below 5° C.; (c) Tape Hardware: 5° C. in an hour. |
|---|---|
| Non-operational temperature limits | −40 to 65° C. |
| Non-operational humidity limits | 5% to 95% relative humidity with 33° C. maximum dew point with atmosphere non-condensing at all times |
| Maximum non-operational altitude | 12,000 meters |
| Maximum operational altitude | 3000 meters |
| Operational altitude de-rating <35° C. maximum rating | Maximum temperature is reduced 1° C./300 meter above 950 meters |
| 40° C. maximum rating | Maximum temperature is reduced 1° C./175 meter above 950 meters |
| ≥45° C. maximum rating | Maximum temperature is reduced 1° C./125 meter above 950 meters |

Another notional example of specified environmental conditions for a particular IT component is provided in TABLE 2. The specification includes 35° C. continuous operation with 45° C. excursion capability (fresh air cooling).

TABLE 2

|  | Continuous Operation | ≤10% of operational hours | ≤1% of operational hours |
|---|---|---|---|
| Temperature ranges (for altitude ≤950 meters) | 10 to 35° C. with no direct sunlight on the equipment | 5 to 10° C., and 35 to 40° C. with no direct sunlight on the equipment | −5 to 5° C., and 40 to 45° C. with no direct sunlight on the equipment |
| Humidity percent ranges | 10% to 80% relative humidity with 29° C. maximum dew point | 5% to 85% relative humidity with 29° C. maximum dew point | 5% to 90% relative humidity with 29° C. maximum dew point |

In the following detailed description of exemplary embodiments of the disclosure, specific exemplary embodiments in which the disclosure may be practiced are described in sufficient detail to enable those skilled in the art to practice the disclosed embodiments. For example, specific details such as specific method orders, structures, elements, and connections have been presented herein. However, it is to be understood that the specific details presented need not be utilized to practice embodiments of the present disclosure. It is also to be understood that other embodiments may be utilized, and that logical, architectural, programmatic, mechanical, electrical and other changes may be made without departing from the general scope of the disclosure. The following detailed description is, therefore, not to be taken in a limiting sense, and the scope of the present disclosure is defined by the appended claims and equivalents thereof.

References within the specification to "one embodiment," "an embodiment," "embodiments", or "one or more embodiments" are intended to indicate that a particular feature, structure, or characteristic described in connection with the embodiment is included in at least one embodiment of the present disclosure. The appearance of such phrases in various places within the specification are not necessarily all referring to the same embodiment, nor are separate or alternative embodiments mutually exclusive of other embodiments. Further, various features are described which may be exhibited by some embodiments and not by others. Similarly, various requirements are described which may be requirements for some embodiments but not other embodiments.

It is understood that the use of specific component, device and/or parameter names and/or corresponding acronyms thereof, such as those of the executing utility, logic, and/or firmware described herein, are for example only and not meant to imply any limitations on the described embodiments. The embodiments may thus be described with different nomenclature and/or terminology utilized to describe the components, devices, parameters, methods and/or functions herein, without limitation. References to any specific protocol or proprietary name in describing one or more elements, features or concepts of the embodiments are provided solely as examples of one implementation, and such references do not limit the extension of the claimed embodiments to embodiments in which different element, feature, protocol, or concept names are utilized. Thus, each term utilized herein is to be given its broadest interpretation given the context in which that term is utilized.

FIG. 1 depicts a simplified functional block diagram of data center, and in particular a modular data center (MDC) 100 having IT components such as information handling systems (IHSs) 102 and management system 104. Management system 104 controls interior environmental conditions in MDC 100 to facilitate operating state changes of individual IT components or equipment such as IHSs 102. In addition, management system 104 triggers the operating state change when specified interior environmental conditions are achieved. Within the general context of IHSs, IHS 102 may include any instrumentality or aggregate of instrumentalities operable to compute, classify, process, transmit, receive, retrieve, originate, switch, store, display, manifest, detect, record, reproduce, handle, or utilize any form of information, intelligence, or data for business, scientific, control, entertainment, or other purposes. For example, IHS 102 may be a server, blade server, rack-mounted server, rack-mounted data storage, or other rack-mounted IT equipment. IHS 102 may include random access memory (RAM), one or more processing resources such as a central processing unit (CPU) or hardware or software control logic, read only memory (ROM), and/or other types of nonvolatile memory. Additional components of the IHS 102 may include one or more disk drives, one or more network ports for communicating with external devices as well as various input and output (I/O) devices, such as a keyboard, a mouse, and a video display. The IHS 102 may also include one or more buses operable to transmit communications between the various hardware components. In one or more embodiments, IHS 102 is rack-mounted to provide computing, communication and storage functionality in mobile MDC 100.

IHS 102 includes a network interface, depicted as network interface controller (NIC) 106. NIC 106 is communicatively connected to network 108. Remote device systems 110 are also communicatively connected to network 108. NIC 106 enables IHS 102 and/or components within IHS 102 to communicate and/or interface with other devices, services, and components that are located external to IHS 102. IHS 102 receives IHS updates and work requests from remote device systems 110 via network 108. These devices, services, and components can interface with IHS 102 via an external network, such as network 108, using one or more communication protocols that include transport control protocol (TCP/IP) and network block device (NBD) protocol. Network 108 can be a local area network, wide area network, personal area network, and the like, and the connection to and/or between network 108 and IHS 102 can be wired, wireless, or a combination thereof. For purposes of discussion, network 108 is indicated as a single collective component for simplicity. However, it should be appreciated that network 108 can comprise one or more direct connections to other devices as well as a more complex set of interconnections as can exist within a local area network or a wide area network, such as the Internet.

A processor subsystem 112 is coupled to system memory 114 via system interconnect 116. System interconnect 116 can be interchangeably referred to as a system bus, in one or more embodiments. System interconnect 116 may represent a variety of suitable types of bus structures, e.g., a memory bus, a peripheral bus, or a local bus using various bus architectures in selected embodiments. For example, such architectures may include, but are not limited to, Micro Channel Architecture (MCA) bus, Industry Standard Architecture (ISA) bus, Enhanced ISA (EISA) bus, Peripheral Component Interconnect (PCI) bus, PCI-Express bus, HyperTransport (HT) bus, and Video Electronics Standards Association (VESA) local bus. For the purpose of this disclosure, system interconnect 116 can also be a Double Data Rate (DDR) memory interface. The system memory 114 can either be contained on separate, removable dual inline memory module (RDIMM) devices or system memory 114 can be contained within persistent memory devices (NVDIMMs). For example, the NVDIMM-N variety of NVDIMMs contain both random access memory, which can serve as system memory 114, and non-volatile memory. It should be noted that other channels of communication can be contained within system interconnect 116, including but not limited to inter-integrated circuit (i2c) or system management bus (SMBus). System interconnect 116 communicatively couples various system components. Examples of system components include replaceable local storage resources 118 (illustrated as "Storage Resources") such as solid state drives (SDDs) and hard disk drives (HDDs). Software and/or firmware modules and one or more sets of data that can be stored on local storage resources 118 and be utilized during operations of IHS 102. Specifically, in one embodiment, system memory 114 can include therein a plurality of such modules, including cooling mode and equipment operating state (CM/EOS) application 119, other application(s) 120, operating system (OS) 121, a firmware interface 122 such as basic input/output system (BIOS) or Uniform Extensible Firmware Interface (UEFI), and platform firmware (FW) 123. These software and/or firmware modules have varying functionality when their corresponding program code is executed by processor subsystem 112 or secondary processing devices within IHS 102. For example, other application(s) 120 may include a word processing application and a presentation application, among other applications. System memory 114 can include computer data structures and data values, such as specification data structure 125 that contains specified environmental conditions for each activation state. These data structures and values can be used by applications (119, 120).

IHS 102 further includes one or more input/output (I/O) controllers 128 that support connection by and processing of signals from one or more connected input device/s 130, such as a keyboard, mouse, touch screen, or microphone. I/O controllers 128 also support connection to and forwarding of output signals to one or more connected output devices 132, such as a monitor or display device or audio speaker(s). Additionally, in one or more embodiments, one or more device interfaces 134, such as an optical reader, a universal serial bus (USB), a card reader, Personal Computer Memory Card International Association (PCMCIA) slot, and/or a high-definition multimedia interface (HDMI), can be associated with IHS 102. Device interface(s) 134 can be utilized to enable data to be read from or stored to corresponding removable storage device/s 136, such as a compact disk (CD), digital video disk (DVD), flash drive, or flash memory card. In one or more embodiments, device interface(s) 134 can further include general purpose I/O interfaces such as inter-integrated circuit ($I^2C$), system management bus (SMB), and peripheral component interconnect (PCI) buses.

In one or more embodiments, enclosure structure 141 is provided by volumetric container 143. In one or more alternate embodiments, enclosure structure 141 is a building that houses a data center. Enclosure structure 141 refers to a barrier that encompasses an IT space for internally directing supply air. Environmental subsystem 144, managed by management controller 138 of management system 104, provides cooling air to meet the cooling requirements of IHSs 102 in one or more zones 140a, 140z defined within enclosure structure 141 of MDC 100. In some instances, environmental subsystem 144 warms the supply air to a specified level required by one or more of the IT components at one or more associated operating states. The cooling/heating requirements can include specified temperature and humidity ranges for startup, standby, and operation of IHSs 102. Operating outside of these ranges can degrade the service life or prevent effective operation of IHSs 102. Environmental subsystem 144 can include stand-alone cooling and heating unit(s) 145, which include heater(s) 142, air handling unit(s) (AHU(s)) 146 and evaporative/mechanical cooling subsystems 148. Compressor(s) 149 in evaporative/mechanical cooling subsystems 148 provide heat transfer for environmental subsystem 144. AHU(s) 146 have mode actuators 150 that configure air flow for closed loop recirculation, open loop venting with cooling by outside air, or a mixed mode with a partial recirculation of air. The air is moved by air mover(s) 151 of AHU(s) 146. Management controller 138 can include some or all of the components and functionality described above for IHSs 102. In one or more embodiments, management controller 138 acts as supervisory controller to respective control unit controllers 152 that control corresponding cooling and heating unit(s) 145 of environmental subsystem 145. In one or more embodiments, management controller 138 executes cooling mode and equipment operating state (CM/EOS) application 119 to enable MDC 100 to provide the functionality described herein. In one or more embodiments, IHSs 102 can communicate cooling requirements to management controller 138, via device interface 153, based on values provided by power consumption monitor 154, rack pressure sensor 156a, rack humidity sensor 156b, and rack temperature sensor 156c. For example, the cooling requirement can indicate a temperature set point and a current temperature of the supply air and a current temperature of the return air. As another example, the cooling requirement can indicate a current heat load being produced by IHSs 102. In one or more embodiments, management controller 138 can determine cooling requirements based in part on outside environmental sensors, depicted as outside pressure sensor 158a, outside temperature sensor 160a, and outside humidity sensor 162a. In one or more embodiments, management controller 138 can determine cooling requirements for first zone 140a based in part on cold aisle (CA) environmental sensors in first zone 140a, depicted as CA pressure sensor 158b, CA temperature sensor 160b, and CA humidity sensor 162b. In one or more embodiments, management controller 138 can determine cooling requirements for first zone 140a based in part on hot aisle (HA) environmental sensors in first zone 140a, depicted as HA pressure sensor 158c, HA temperature sensor 160c, and HA humidity sensor 162c.

In one or more embodiments, management controller 138 can determine cooling requirements for second zone 140z based in part on CA environmental sensors in second zone 140z, depicted as CA pressure sensor 158d, CA temperature sensor 160d, and CA humidity sensor 162d. In one or more embodiments, management controller 138 can determine cooling requirements for second zone 140z based in part on HA environmental sensors in second zone 140z, depicted as HA pressure sensor 158e, HA temperature sensor 160e, and HA humidity sensor 162e.

IHSs 102 can be configured differently and be utilized at different times. For example, one IHS 102 can include data storage hard drives that have specified temperature ranges for different operational states, including for (i) when inactive, (ii) when powered up to standby but without starting moving parts with in the hard drives, and (iii) when made operational. For example, a minimum temperature can be specified for when the IHS is inactive. That minimum temperature can be much lower than the temperature required for the IHS to be in an operating state. For example, thermal stresses between heat-generating components and non-heating generating components at a low temperature can create mechanical expansion stresses that cause damage. For another example, moving components can rely on a type of lubricant that solidifies below a certain temperature. Equipment that relies on the lubricant would have environmental specification that require the temperature for an active operating state to be higher than this certain temperature where the lubricant becomes solid. A temperature change rate can be specified that dictates a maximum change in temperature as a function of time that is allowed in a particular operating state to avoid differential thermal expansions or contractions that can cause damage to the IHS. Another IHS 102 can include solid state drives with no moving parts, which thus enables a larger acceptable temperature range for operating.

According to aspects of the present disclosure, management controller 138 can adjust estimates of temperature values and temperature set points to compensate for variabilities and margins of error. For example, a temperature set point can be set within a narrower range than a specified temperature range to provide confidence that the temperature of the supply air is within the specified range.

Based on workload requirements, particular ones of IHSs 102 can be inactive or active. Due to upgrades or maintenance, IHSs 102 can be installed or replaced. During startup of environmental system 144, IHSs 102 and other IT components requiring cooling can be in an inactive/OFF state, such as during initial commissioning or when otherwise bringing MDC 100 to an operational status. Managing controller 138 ensures that switching IHSs 102 on can be done in a customized, individualized manner, as environmental conditions are brought within specified ranges by environmental subsystem 144.

In one or more embodiments, management system 104 controls infrastructure support to IHSs 102 in MDC 100, including control of environmental subsystem 144, network subsystem 166, power distribution subsystem 168, security subsystem 170, and fire suppression subsystem 172 ("illustrated as Fire"). Management system 104 can be assigned to control these functions within a particular volumetric container 143. In one or more embodiments, management system 104 controls these functions within an IT space within one or more rooms of a facility. In one or more embodiments, management system 104 is part of IHS 102. In one or more embodiments, management system 104 is part of environmental subsystem 144. In one or more embodiments, management system 104 is at least partially provided by remote device system 110. In one or more embodiments, management controller 138 is a programmable logic controller (PLC) that is connected to the other subsystems via one or more interconnects and communication protocols. Management controller 138 interfaces with IHSs 102, the infrastructure subsystems (144, 166, 168, 170, and 172) and communicates to a network operations center or building management system. According to the present disclosure, management controller 138 controls environmental subsystem 144 to individually accommodate specified environmental conditions for IT components such as IHSs 102. Management controller 138 executes CM/EOS application 119 to enable management system 104 to provide functionality of aspects of the present disclosure. Management controller 138 monitors sensors (158a-158e, 160a-160e, and/or 162a-162e), which detect the interior and outside air pressure, temperature, and humidity values. Management controller 138 determines that a request is received for one or more particular IT components to change in operating state. For example, an IT component can be a plug and play device that becomes known via system interlink 116 as available to MDC 100. IHS 102 can request confirmation from management controller 138 that environmental conditions allow activating the newly installed plug and play device. As another example, a remote device system 110 can send notice of an increase in workload to MDC 100 that prompts management controller 138 to start additional IHSs 102. Management controller 138 accesses specification data structure 125 and determines at least a first temperature range specified in specification data structure 125 for the IT component that is scheduled to transition into a first operational state. Management controller 138 adjusts a temperature set point of supply air provided by environmental subsystems 144 to the first IT component to be within the first temperature range. Management controller 138 determines whether the temperature of the supply air provided to the first IT component is at/within the first temperature range. In response to determining that the interior air temperature is within the first temperature range, management controller 138 enables or triggers activation of the first IT component to the first operational state.

In one or more embodiments, environmental subsystem 144 detects, via input from air sensors, an outside ambient condition as being in one of multiple environmental condition ranges. In one or more embodiments, the environmental condition ranges are defined on a psychrometric chart that is tailored for a location of the data center. In an illustrative embodiment, environmental subsystem 144 is equipped to operate in one of four cooling modes defined by environmental condition ranges that are mutually exclusive and which cover the full range of environmental conditions that MDC 100 should encounter at the operational location. First, a "normal mode" provides open loop cooling using outside air. Second, a "mixed mode" provides mixing outside air with recirculated return air that is warmed by the data center. Third, a "mechanical trim mode" includes mixing of outside air with recirculated return air. Fourth, a "closed mode" recirculates all return air with cooling provided by the mechanical cooling subsystem. In one or more embodiments, fewer modes may be required for a particular location. Other environmental considerations such as the amount of contaminants in the outside air can affect mode selection, including reverting to closed loop cooling. The ranges of environmental conditions are based at least on outside air temperature and outside air humidity.

Figure 2:
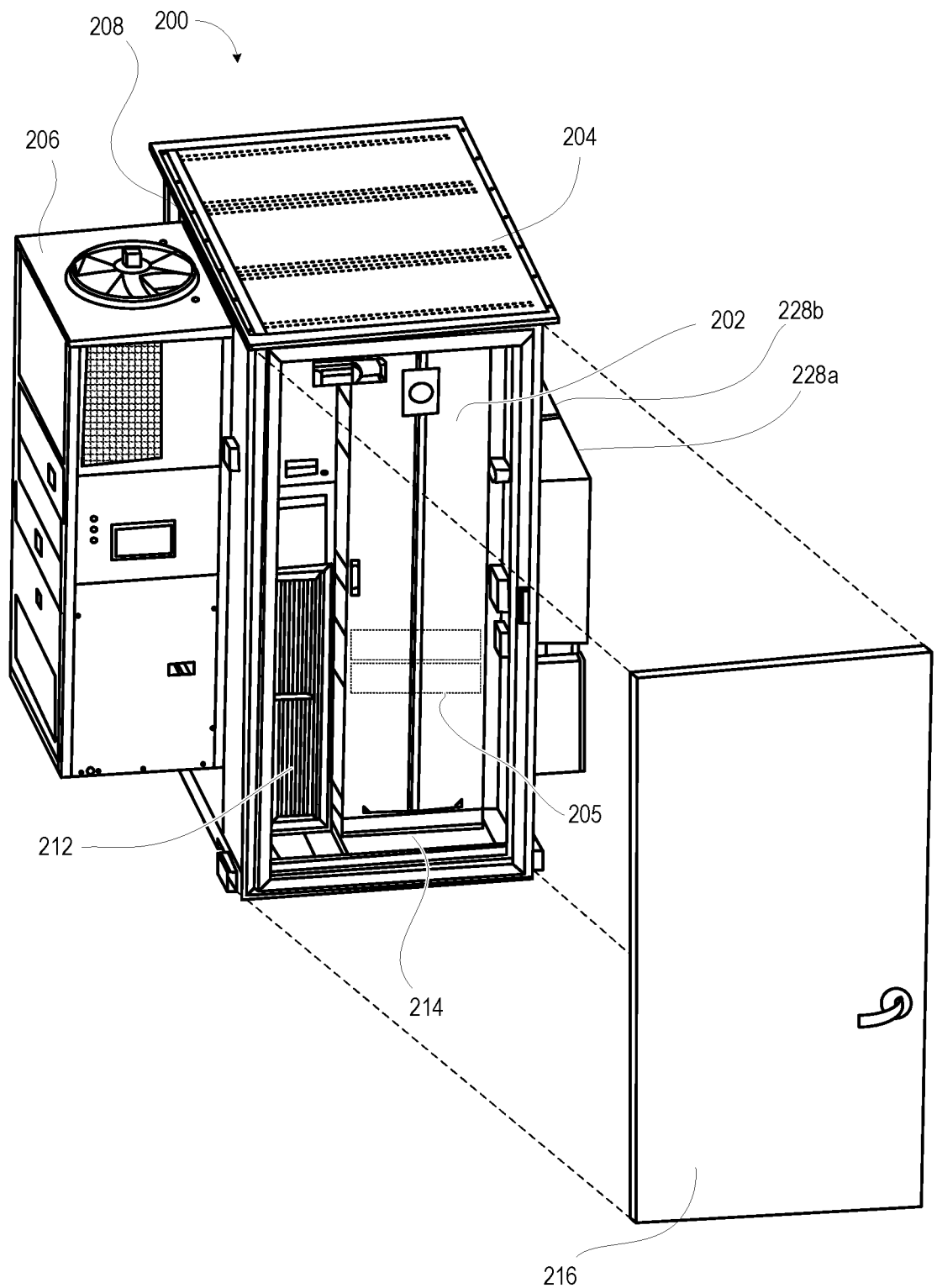
FIG. 2 depicts a perspective top left view of an example MDC, according to one or more embodiments.

FIG. 2 depicts a perspective, top left view of example modular data center (MDC) 200. MDC 200 can be placed in locations where data capacity is needed. MDC 200 is an example implementation of MDC 100 (FIG. 1). MDC 200 is composed of purpose-engineered modules and components that offer scalable data center capacity with multiple power and cooling options. Modular edge data centers (MEDCs) are generally smaller MDC facilities that extend the edge of the network to deliver cloud computing resources and cached streaming content to local end users. MEDCs that have only one or two racks for IT are also referred to as micro MDCs. Minimizing a footprint of an MEDC, and especially for a micro MDC, enables use in space-constrained applications. Rack Information Handling System (RIHS) 202 is positioned within volumetric container 204. RIHS 202 contains heat-generating IT components 205 such as IHSs 102 (FIG. 1). Cooling and heating unit 206 is mounted to rear external wall 208 of MDC 200 and directs air internally through volumetric container 204 via air redirection structure 212. Supply air is directed to cold aisle 214 to cool RIHS 202. Left personnel access door 216 is depicted as removed from volumetric container 204. Equipment panels 228a-228b are attached to a front side of volumetric container 204.

Figure 3:
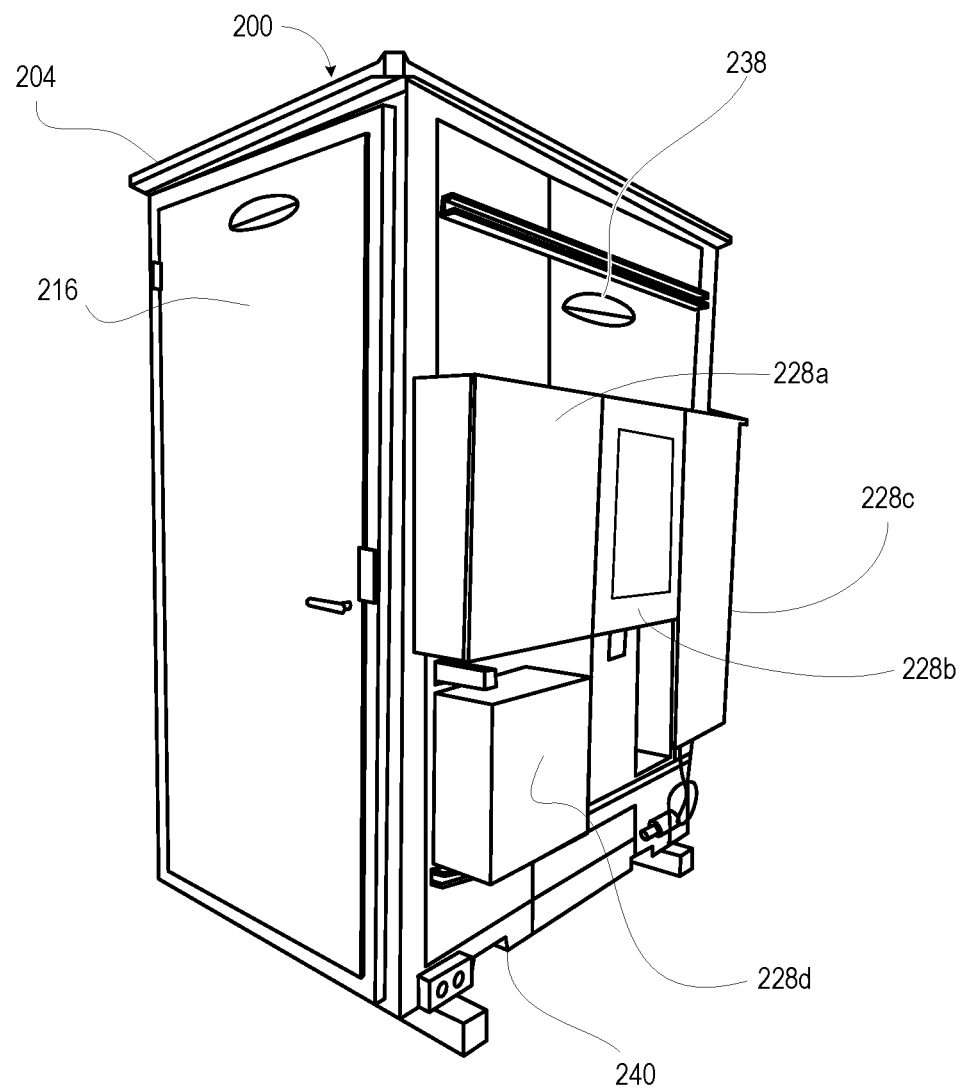
FIG. 3 depicts a perspective right front view of the example MDC of FIG. 2, according to one or more embodiments.

FIG. 3 depicts a perspective right front view of example MDC 200. Left personnel access door 216 is depicted in a closed position. Equipment panels 228a-228d provide a degree of access to network, security, power, and environmental subsystems. Base 240 of volumetric container 204 includes pallet-like features for movement of MDC 200 by forklift vehicle.

Figure 4:
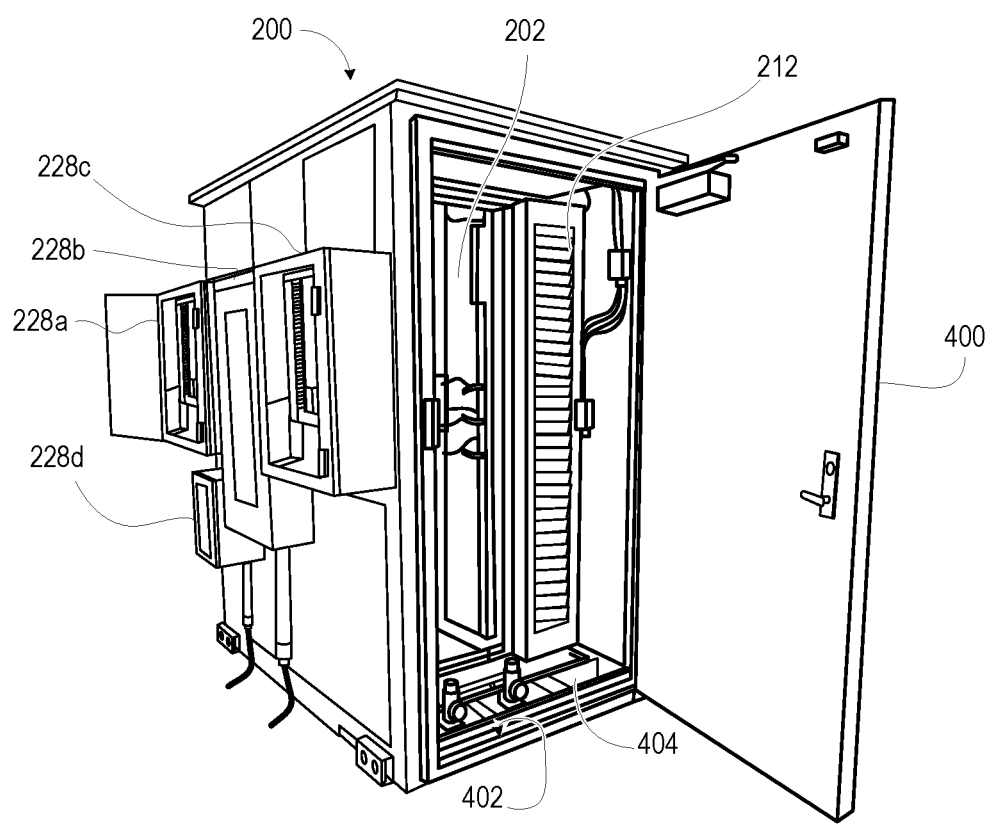
FIG. 4 depicts a perspective right rear view of the example MDC of FIG. 2, according to one or more embodiments.

FIG. 4 depicts a perspective right rear view of example MDC 200 with right personnel access door 400 open. When right personnel access door 400 is closed in right door opening 402, air redirection structure 212 draws return air from hot aisle 404 back to cooling and heating unit 206 (FIG. 2).

Figure 5:
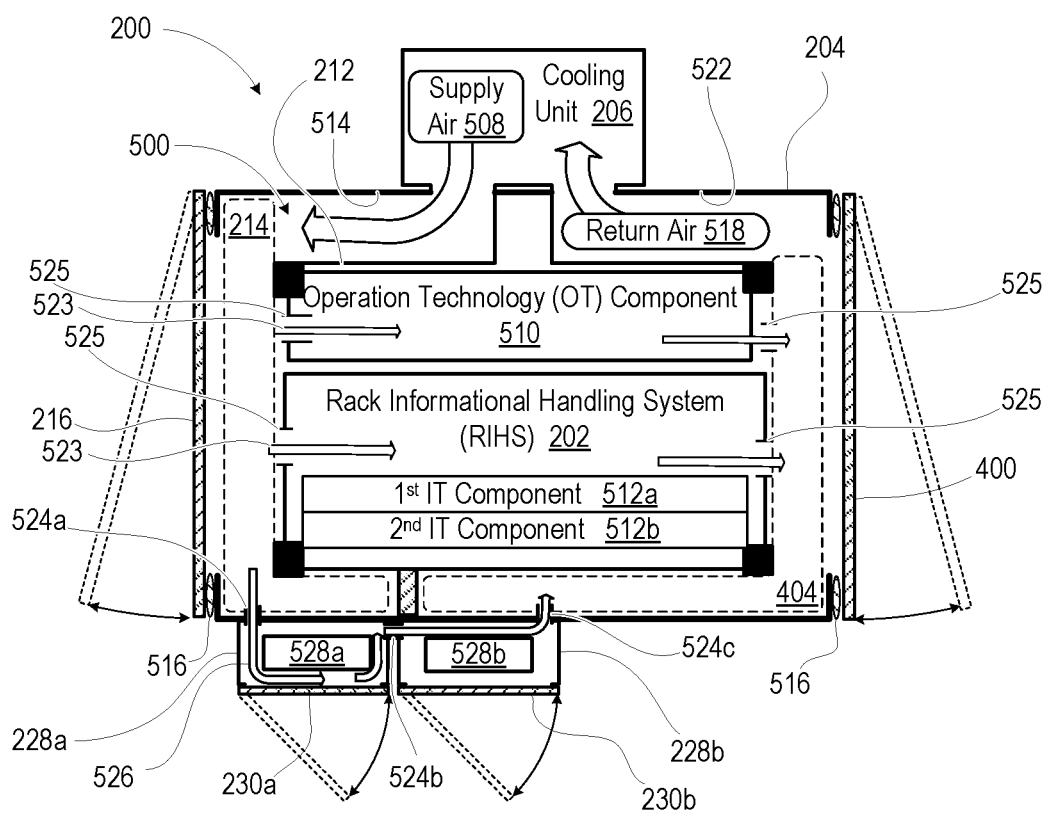
FIG. 5 depicts a top diagrammatic view of air flow patterns in the example MDC, according to one or more embodiments.

FIG. 5 depicts a top diagrammatic view of air flow patterns 500 in example MDC 200 with left and right access doors 216, 400 in a closed position. Cooling and heating unit 206, which is exteriorly coupled to volumetric container 204, provides supply air 508. Cooling and heating unit 206 can prepare supply air 508, which can include recirculated air, outside air, or mixed air. Cooling and heating unit 206 warms, cools, dehumidifies, or humidifies the air, as required for operation technology (OT) components 510 and information technology (IT) components 512a-512b in RIHS 202. IT components 512a-512b can have different specified temperature, humidity, and temperature change rate for different operating states, such as non-operational, startup, sleep, standby, and operating/operational states. For example, cooling and heating unit 206 can cool air using direct evaporative cooling or mechanical cooling. Cooling and heating unit 206 pressurizes supply air 508 that is directed by supply air plenum 514 of air redirection structure 212 to cold aisle 214. During normal operation, left and right access doors 216, 400 are sealed with door seals 516 to prevent loss of cooling air. Cooling and heating unit 206 draws return air 518 from hot aisle 404. Return air plenum 522 of air redirection structure 212 directs the return air to cooling and heating unit 206. Cooling and heating unit 206 creates a lower pressure within hot aisle 404 than cold aisle 214. As a result of the pressure differential, cooling air 523 is passively drawn through inlet and outlet air passages 525 in OT components 510 and RIHS 202.

Equipment panel 228a-228b are air cooled by pneumatic passages 524a-524c that respectively provide fluid communication of supply air 526 between: (i) cold aisle 214 and equipment panel 228a; (ii) equipment panels 228a-228b; and (iii) equipment panel 228b and hot aisle 404. IT components 528a-528b in respective equipment panels 228a-228b can have specified environmental conditions for particular operating states.

Figure 6:
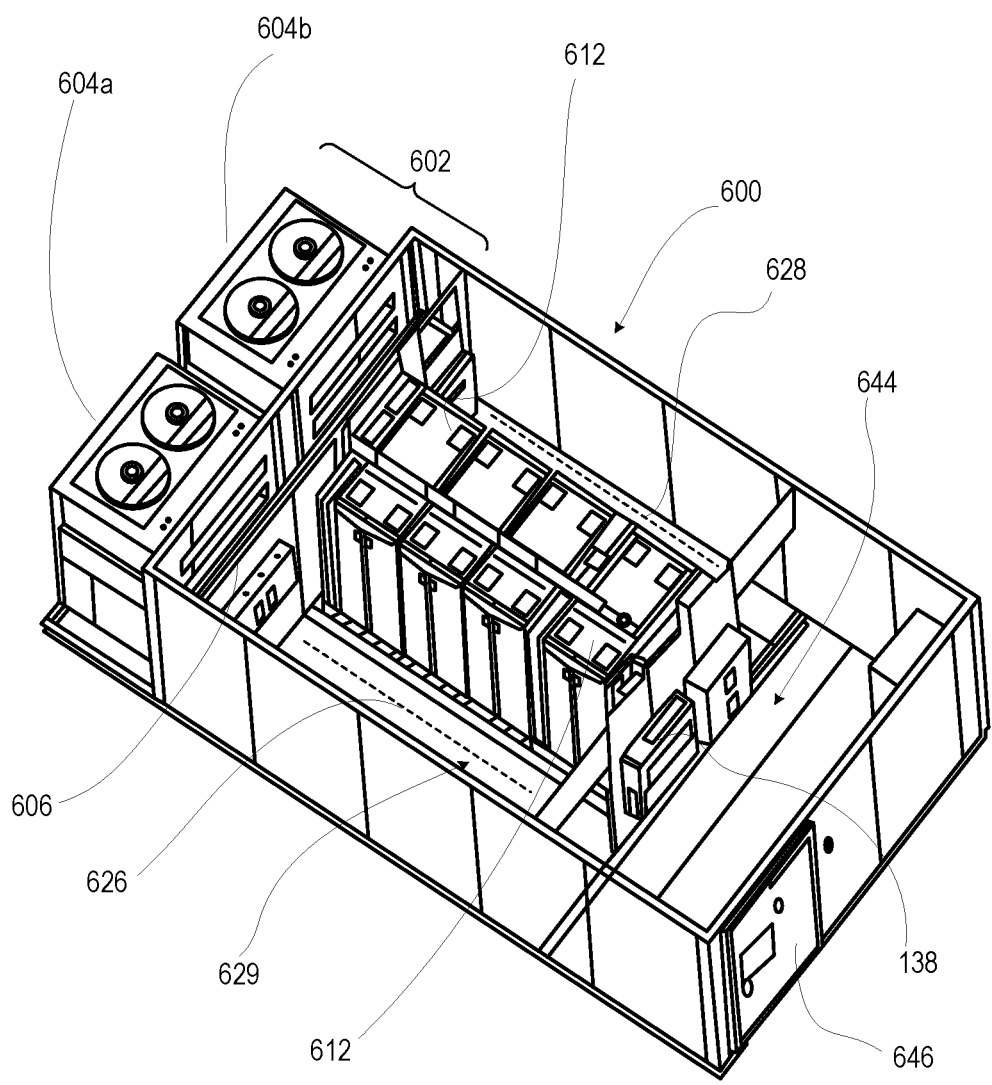
FIG. 6 depicts a three-dimensional, top view of an example MDC that has an information technology (IT) compartment and a utility room, according to one or more embodiments.

FIG. 6 depicts a three-dimensional, top view of example MDC 600 that has IT compartment 629 and utility room 644. IT compartment 629 includes a longitudinal row of IT components 612 between cold and hot aisles 626, 628. Dual-AHU air handling system 602 of MDC 600 includes two forward-mounted or aft-mounted AHUs 604a, 604b. AHUs 604a, 604b exchange cooling air via air redirection structure 606 with the IT compartment 629 and utility room 644 via cold and hot aisles 626, 628. Utility room 644 includes management controller 138 that monitors and controls access door 646 to utility room 644. MDC 600 is an example MDC. However, aspects of the present disclosure can be applied to data centers housed in institutional buildings, larger MDCs within a single volumetric container, smaller MDCs having one or two racks within a small volumetric container, and MDCs that include multiple volumetric enclosures.

Figure 7:
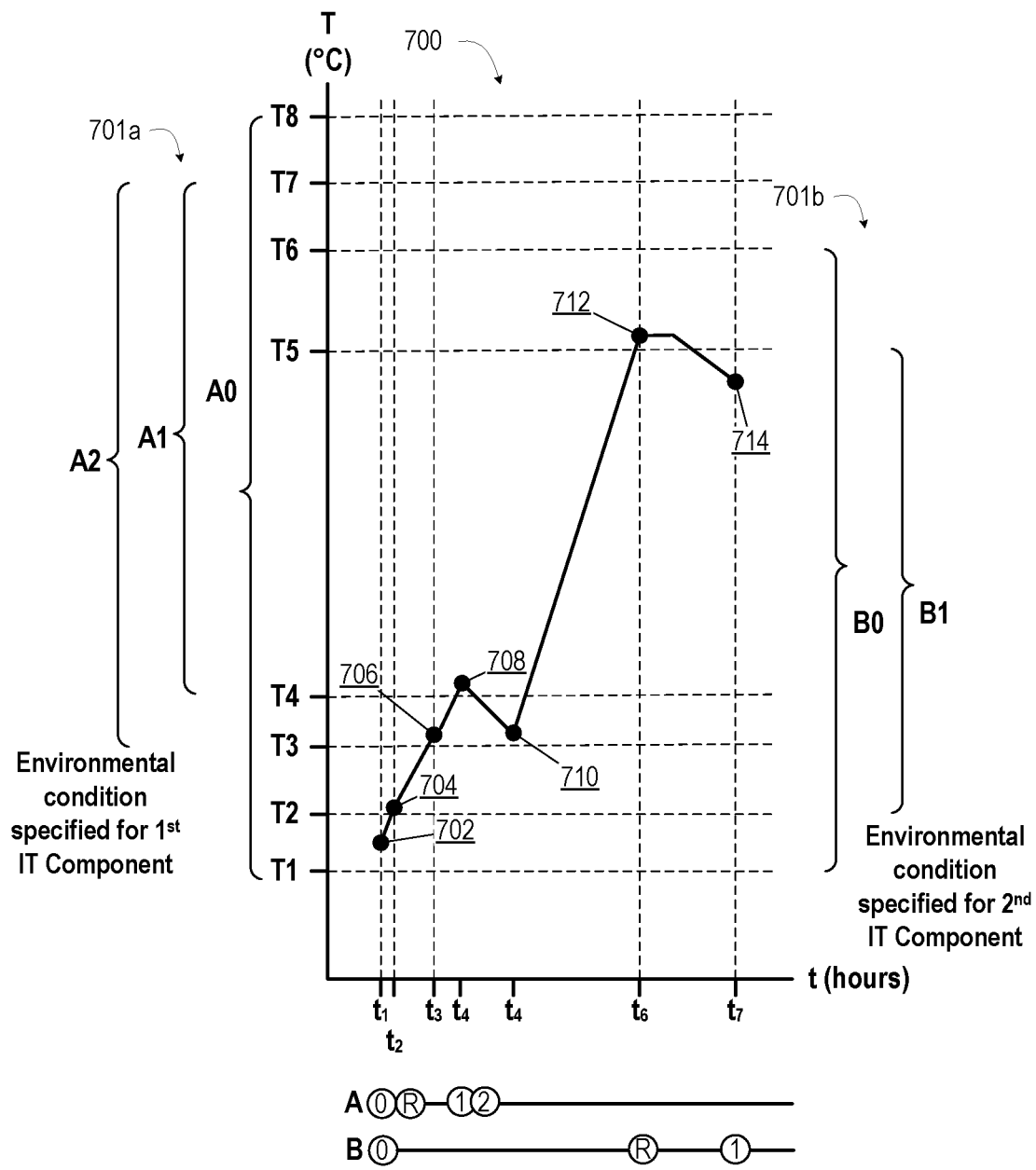
FIG. 7 depicts a graphical plot of internal air temperature in a data center, according to one or more embodiments.

FIG. 7 depicts a graphical plot 700 of an internal air temperature in a data center. The data center can be one of MDC 100 (FIG. 1), 200 (FIG. 2), and 600 (FIG. 6). Management controller 138 (FIG. 1) adjusts the temperature set point in response to requests to change an operating state of a first and a second IT component that have different specified operating temperature ranges. For clarity, only environmental condition specifications 701a (A0-A2) and 701b (B0-B1) for two IT components are annotated, but it is appreciated that aspects of the present disclosure can apply to a large number of IT components that can have differing temperature and humidity requirements. First IT component has temperature specifications: (i) Inactive state (A0): temperature range T1-T8; (ii) first operating state/startup (A1): temperature range T4-T7; and operational state (A2): temperature range T3-T7. Second IT component has temperature specifications: (i) inactive state/OFF (B0): temperature range T1-T6; and (ii) active state/ON (B1): temperature range T2-T5.

At time t1, first and second IT components are both inactive, i.e., in states A0 and B0. An internal air temperature in the data center is between temperatures T1-T2. The internal air temperature can be sensed within or on a surface of the IT components, in an IT airspace proximate to the IT components, and/or within an air passage that provides supply air to the IT components. Annotated point 702 denotes a starting point where management system 138 (FIG. 1) becomes active (i.e., where the management system is powered or turned on to begin modulating the temperature and humidity inside of the MDC). At this point, the internal temperature of the MCD is out of the desired range for operation of either of the IT components and is thus appropriate only for the first and second IT components to remain inactive.

At time t2, the internal air temperature has risen to annotated point 704 that is greater than temperature T2 but less than temperature T3. Management controller 138 (FIG. 1) receives a request to enable a change if the first IT component from the inactive state (A0) to the first operating state (A1). The request can originate, for example, from one of: (i) IHSs 102, remote device system 110 (FIG. 1), or equipment panels 228a-228d (FIG. 3). The power cycling component for the first IT component (not shown) and/or management controller 138 (FIG. 1) receives (from the temperature sensors) the current values of the internal air temperature (measured around the first IT component) and compares that current internal air temperature to the temperature range (T4-T7) within which the first IT component is allowed to enter into the first operating state (A1). Management controller 138 (FIG. 1) determines that the current interior air temperature such as surrounding the first IT component is not within the specified temperature range (T4-T7) to support the change in operating state. Management controller 138 (FIG. 1) increments/decrements the temperature set point for the MDC interior upwards/downward at a rate that is within the allowable temperature gradient or temperature change rate (not shown).

Notably, the temperature at time t2 is within the specified temperature range for the second IT component to change to active state/ON (B1). However, management controller 138 (FIG. 1) has received a request to activate second IT component. For example, second IT component can be a backup server that is not currently needed to handle the workload of the data center.

At time t3, the internal air temperature has risen to annotated point 706 that is above temperature T3, less than temperature T4, but is not yet within the temperature range specified for the first operating state (A1) of the first IT component. At time t4, the internal air temperature has risen to annotated point 708 that is above temperature T4 but less than temperature T5. This internal air temperature is within the temperature range specified for the first operating state (A1) of the first IT component. The first IT component is allowed to startup in the first operating state and then to transition to the second operating state (A2) for operation.

At time t5, the internal air temperature has dropped to annotated point 710 that is above temperature T3 but less than temperature T4, which is within the temperature range (T3-T7) specified for the second operating state (A2) of the first IT component, but outside the temperature range (T4-T7) for the first operating state (A1). For example, the internal air temperature could be allowed to drop for economical operation with a cold outside temperature. As another example, the internal air temperature could be cooled to a lower temperature set point in order to handle a larger cooling requirement of the data center. The internal air temperature (measured within the airspace surrounding the first IT component) is thus within the temperature range specified for the second operating state (A2) of the first IT component. For example, the first IT component, when operating, can generate enough movement and surface heat to be exposed to a lower temperature than what is preferred for startup. In this scenario, the temperature set point is incremented further upward.

At time t6, the internal air temperature has risen to annotated point 712 that is above temperature T5 but less than temperature T6. Annotated point 712 is within the temperature range specified for any operating state (A0-A2) of the first IT component and the inactive state (B0) for the second IT component. Annotated point 172 is not within the temperature range specified for the first operating state (B1) for the second IT component. For example, the internal air temperature could be allowed to rise for economical operation in response to a warming outside temperature. At time t6, management controller 138 (FIG. 1) has not received a request to activate the second IT component to the first operating state/ON (B1). Management controller 138 (FIG. 1) reduces the temperature set point in increments to enable the requested operating state change for the second IT component, while staying within the range for the continued operation of the first IT component in its current operational state (A2).

At time t7, the internal air temperature has been lowered to annotated point 714 that is above temperature T4 but less than temperature T5, which is within the temperature range specified for any operating state (A0-A2) of the first IT component and any operating state (B0-B1) for the second IT component. The second IT component is allowed to change operating state to the first operating state/ON (B1).

FIGS. 8A-8D (FIG. 8) depict a method 800 for controlling interior environmental conditions to facilitate operating state changes of individual IT equipment in a data center. The description of method 800 is provided with general reference to the specific components illustrated within the preceding FIGS. 1-6. In at least one embodiment, method 800 can be implemented using management controller 138 (FIG. 1) that operates environmental subsystem 144 (FIG. 1).

Figure 8A:
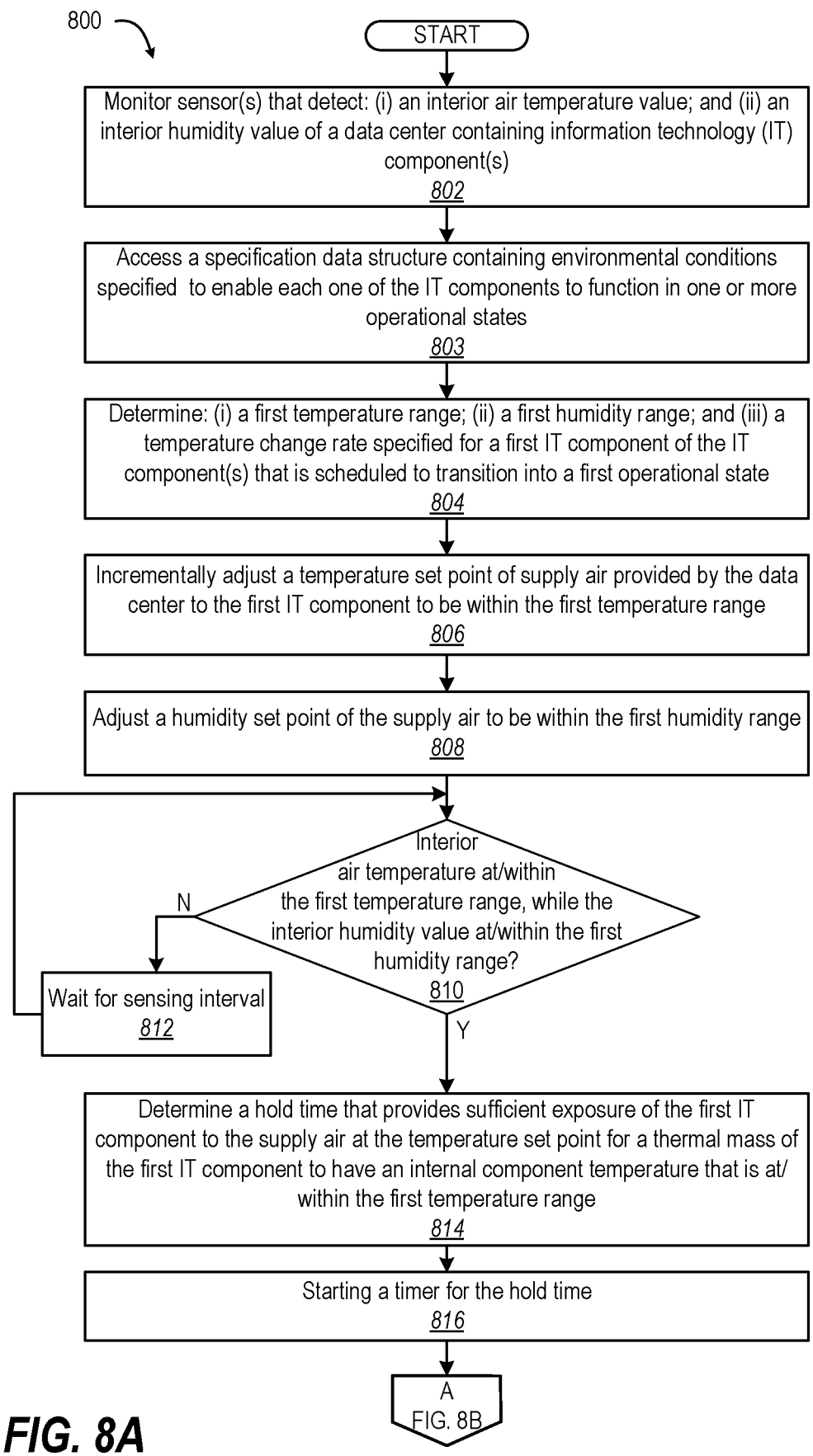
FIGS. 8A-8D (FIG. 8) depict a flow chart illustrating an example method for controlling interior environmental conditions to facilitate operating state changes of individual IT equipment in a data center, according to one or more embodiments.

With reference to FIG. 8A, method 800 includes monitoring sensor(s) that detect: (i) an interior air temperature value; and (ii) an interior humidity value of a data center containing information technology (IT) component(s) (block 802). Method 800 includes accessing a specification data structure containing environmental conditions specified to enable each one of the IT components to function in one or more operational states (block 803). Method 800 includes determining: (i) a first temperature range; (ii) a first humidity range; and (iii) a temperature change rate specified in the specification data structure for a first IT component of the IT component(s) that is scheduled to transition into a first operational state (block 804). In one or more embodiments, the first IT component is scheduled to transition as soon as allowable based on the environmental conditions, which can include immediate transition. In one or more embodiments, the first IT component is scheduled to transition at a particular time that allows adjustment of the environmental conditions. In one or more embodiments, an IT component has two activity states: (i) OFF (inactive); and (ii) ON (active). In one or more embodiments, an IT component has three operating states: (i) non-operation; (ii) startup; and (iii) operation. In one or more embodiments, an IT component has three operating states: (i) non-operation; (ii) standby; and (iii) operation. The first operational state can be one of: (i) ON; (ii) startup; and (iii) standby. Method 800 includes incrementally adjusting a temperature set point of supply air provided by the data center to the first IT component to be within the first temperature range (block 806). The temperature set point is incremented, if necessary, to remain within the temperature change rate, based on closed loop feedback of the interior temperature value. The increment is selected to be less than a specified temperature gradient. For example, the first IT component has a specified temperature gradient or maximum temperature change rate of 20° C. in 1 hour and 5° C. in 15 minutes. In one or more embodiments, method 800 includes incrementing the temperature set point in 1° C. increments that are spaced by 3 minutes until the first temperature range is reached.

Method 800 includes adjusting a humidity set point of the supply air to be within the first humidity range (block 808). A determination is made, in decision block 810, whether the temperature of the supply air provided to the first IT component is at/within the first temperature range, while the interior humidity value is at/within the first humidity range. In response to determining that the interior air temperature is not within the first temperature range while the first humidity value is at/within the first humidity range, method 800 includes waiting for a sensing interval (block 812). The sensing interval is selected based on how quickly the sensed value is expected to change and is selected to reduce computational overhead by the controller. For example, the sensing interval can be 1 second, 10 seconds or 100 seconds. Then method 800 proceeds to decision block 810. In response to determining that the interior air temperature is within the first temperature range while the first humidity value is at/within the first humidity range, in one or more embodiments method 800 includes determining a hold time that provides sufficient exposure of the first IT component to the supply air at the temperature set point for a thermal mass of the first IT component to have an internal component temperature that is at/within the first temperature range (block 814). Method 800 includes starting a timer for the hold time (block 816).

Figure 8B:
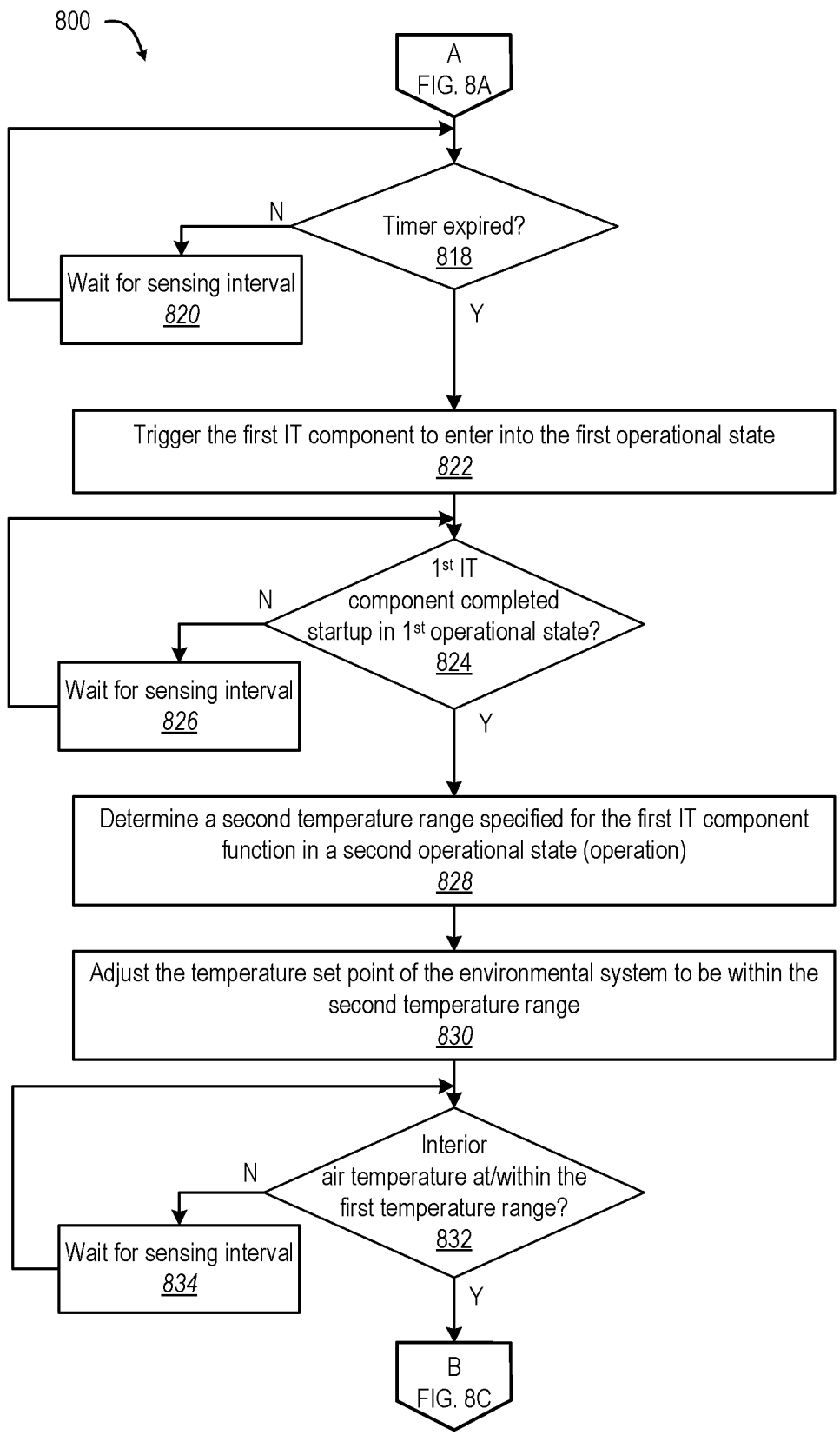

With reference to FIG. 8B, a determination is made, in decision block 818, whether the timer has expired. In response to determining that the timer has not expired, method 800 includes waiting for a sensing interval (block 820). Then method 800 proceeds to decision block 818. In response to determining that the timer has expired, method 800 includes triggering the first IT component to enter into the first operational state (block 822).

In one or more embodiments, a determination is made, in decision block 824, whether the first IT component has completed startup in the first operational state. In response to determining that the first IT component has not completed startup in the first operational state, method 800 includes waiting for a sensing interval (block 826). Then method 800 proceeds to decision block 824. In response to determining that the first IT component has completed startup in the first operational state, method 800 includes determining a second temperature range specified for the first IT component function in a second operational state (operation) (block 828). In one or more embodiments, other criteria, such as a second humidity range and a second temperature change rate, are specified for transitioning the IT component from startup to operating states. Method 800 includes adjusting the temperature set point of the management system to be within the second temperature range (block 830). A determination is made, in decision block 832, whether the temperature of the supply air provided to the first IT component is at/within the first temperature range. In response to determining that the interior air temperature is not within the second temperature range, method 800 includes waiting for a sensing interval (block 834). Then method 800 proceeds to decision block 832.

Figure 8C:
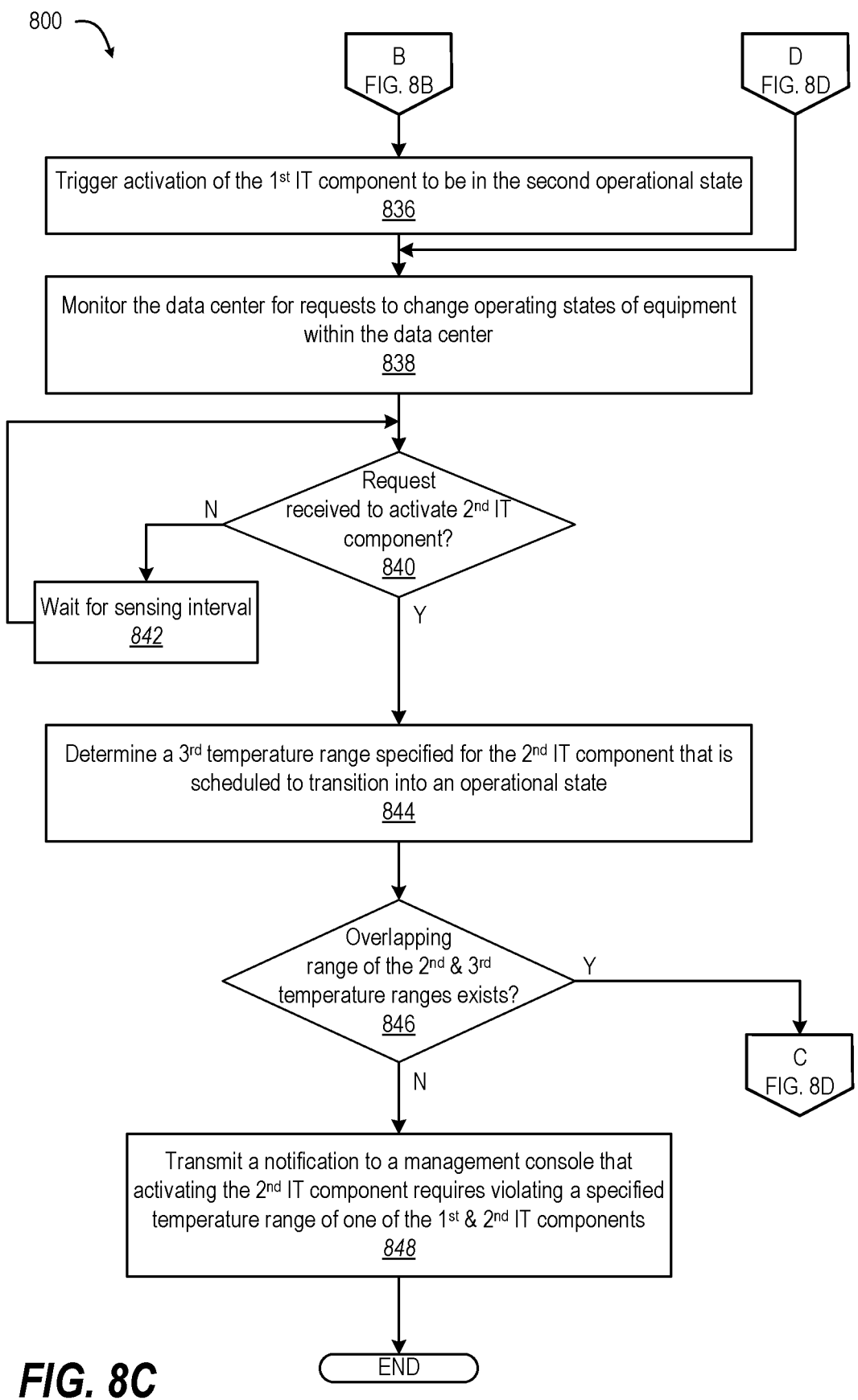

With reference to FIG. 8C, in response to determining that the interior air temperature is within the second temperature range, method 800 includes triggering activation the first IT component to the second operational state (block 836). In one or more embodiments, a second hold time is imposed based on the thermal mass of the first IT component before enabling the first IT component to change to the second operational state.

In one or more embodiments, method 800 includes monitoring the data center for requests to change operating states of equipment within the data center (block 838). A determination is made, in decision block 840, whether a request is received to activate a second IT component of the IT component(s). In response to determining that a request to activate a second IT component is not received, method 800 includes waiting for a sensing interval (block 842). Then method 800 proceeds to decision block 840. In response to determining that a request to activate a second IT component is received, method 800 includes determining a third temperature range specified for the second IT component that is scheduled to transition into an operational state (block 844). Method 800 includes determining, in decision block 846, whether an overlapping range of the second temperature range and the third temperature range exists. In response to determining that an overlapping range does not exist, method 800 includes transmitting a notification to a management console that activating the second IT component requires violating a specified temperature range of one of the first and second IT components (block 848). Then method 800 ends.

Figure 8D:
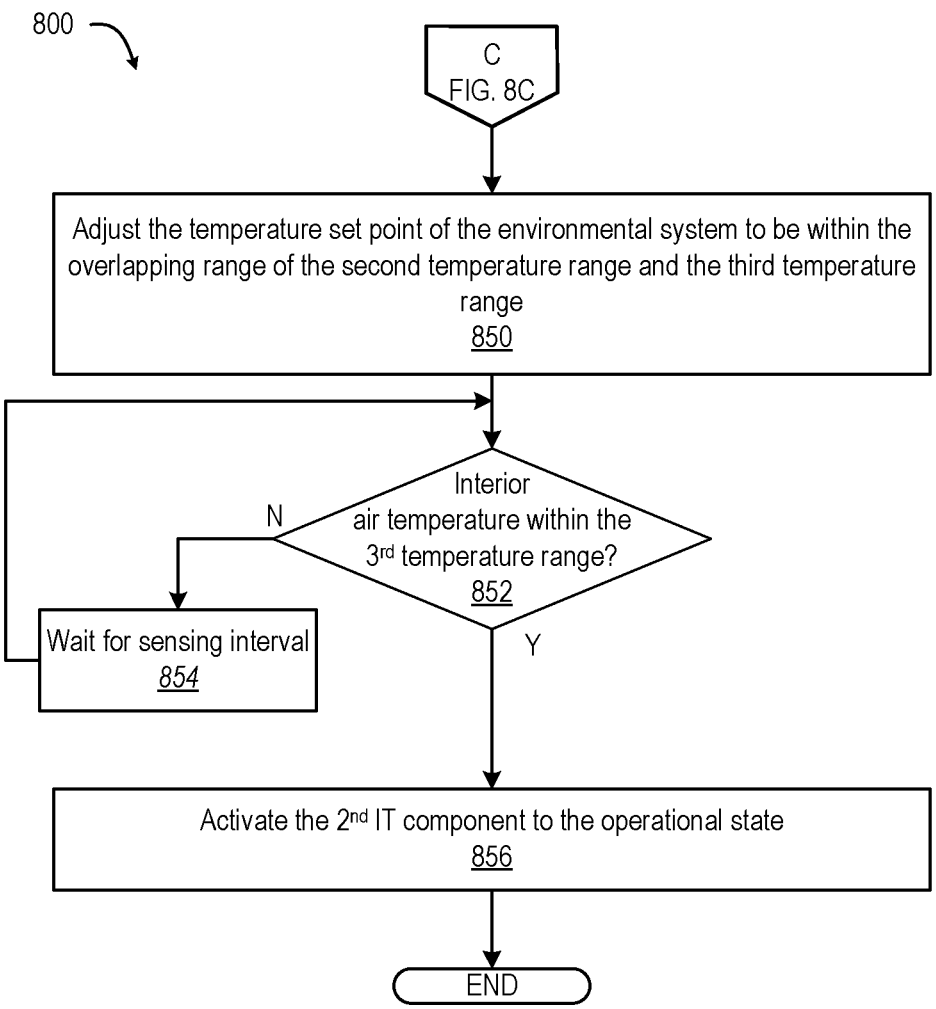

With reference to FIG. 8D, in response to determining in decision block 846 that an overlapping range exists, method 800 includes adjusting the temperature set point of the management system to be within the overlapping range of the second temperature range and the third temperature range (block 850). A determination is made, in decision block 852, whether the temperature of the supply air provided to the first IT component is within the third temperature range. In response to determining that the interior air temperature is not within the third temperature range, method 800 includes waiting for a sensing interval (block 854). Then method 800 proceeds to decision block 852. In response to determining that the interior air temperature is within the third temperature range, method 800 includes activating the second IT component to the operational state (block 856). Then method 800 ends.

In the above described flow charts, one or more of the methods may be embodied in a computer readable medium containing computer readable code such that a series of functional processes are performed when the computer readable code is executed on a computing device. In some implementations, certain steps of the methods are combined, performed simultaneously or in a different order, or perhaps omitted, without deviating from the scope of the disclosure. Thus, while the method blocks are described and illustrated in a particular sequence, use of a specific sequence of functional processes represented by the blocks is not meant to imply any limitations on the disclosure. Changes may be made with regards to the sequence of processes without departing from the scope of the present disclosure. Use of a particular sequence is therefore, not to be taken in a limiting sense, and the scope of the present disclosure is defined only by the appended claims.

Aspects of the present disclosure are described above with reference to flowchart illustrations and/or block diagrams of methods, apparatus (systems) and computer program products according to embodiments of the disclosure. It will be understood that each block of the flowchart illustrations and/or block diagrams, and combinations of blocks in the flowchart illustrations and/or block diagrams, can be implemented by computer program instructions. Computer program code for carrying out operations for aspects of the present disclosure may be written in any combination of one or more programming languages, including an object oriented programming language, without limitation. These computer program instructions may be provided to a processor of a general purpose computer, special purpose computer, such as a service processor, or other programmable data processing apparatus to produce a machine, such that the instructions, which execute via the processor of the computer or other programmable data processing apparatus, performs the method for implementing the functions/acts specified in the flowchart and/or block diagram block or blocks.

One or more of the embodiments of the disclosure described can be implementable, at least in part, using a software-controlled programmable processing device, such as a microprocessor, digital signal processor or other processing device, data processing apparatus or system. Thus, it is appreciated that a computer program for configuring a programmable device, apparatus or system to implement the foregoing described methods is envisaged as an aspect of the present disclosure. The computer program may be embodied as source code or undergo compilation for implementation on a processing device, apparatus, or system. Suitably, the computer program is stored on a carrier device in machine or device readable form, for example in solid-state memory, magnetic memory such as disk or tape, optically or magneto-optically readable memory such as compact disk or digital versatile disk, flash memory, etc. The processing device, apparatus or system utilizes the program or a part thereof to configure the processing device, apparatus, or system for operation.

As will be further appreciated, the processes in embodiments of the present disclosure may be implemented using any combination of software, firmware or hardware. Accordingly, aspects of the present disclosure may take the form of an entirely hardware embodiment or an embodiment combining software (including firmware, resident software, micro-code, etc.) and hardware aspects that may all generally be referred to herein as a "circuit," "module," or "system." Furthermore, aspects of the present disclosure may take the form of a computer program product embodied in one or more computer readable storage device(s) having computer readable program code embodied thereon. Any combination of one or more computer readable storage device(s) may be utilized. The computer readable storage device may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage device would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage device may be any tangible medium that can contain, or store a program for use by or in connection with an instruction execution system, apparatus, or device.

While the disclosure has been described with reference to exemplary embodiments, it will be understood by those skilled in the art that various changes may be made and equivalents may be substituted for elements thereof without departing from the scope of the disclosure. In addition, many modifications may be made to adapt a particular system, device or component thereof to the teachings of the disclosure without departing from the essential scope thereof. Therefore, it is intended that the disclosure not be limited to the particular embodiments disclosed for carrying out this disclosure, but that the disclosure will include all embodiments falling within the scope of the appended claims. Moreover, the use of the terms first, second, etc. do not denote any order or importance, but rather the terms first, second, etc. are used to distinguish one element from another.

The terminology used herein is for the purpose of describing particular embodiments only and is not intended to be limiting of the disclosure. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

The description of the present disclosure has been presented for purposes of illustration and description, but is not intended to be exhaustive or limited to the disclosure in the form disclosed. Many modifications and variations will be apparent to those of ordinary skill in the art without departing from the scope of the disclosure. The described embodiments were chosen and described in order to best explain the principles of the disclosure and the practical application, and to enable others of ordinary skill in the art to understand the disclosure for various embodiments with various modifications as are suited to the particular use contemplated.

What is claimed is:

1. A method of controlling interior environmental conditions to facilitate operating state changes of more than one information technology (IT) components in a data center, the method comprising:
monitoring one or more sensors that detect an interior air temperature value of the data center containing the more than one IT component;
accessing a specification data structure containing environmental conditions specified to enable each one of the more than one IT component to function in one or more operational operating states;
determining, by a controller, a first temperature range specified in the specification data structure for a first IT component of the more than one IT component that is scheduled to transition into a first operational state;
adjusting a temperature set point of supply air provided by the data center to the first IT component to be within the first temperature range, the adjusting comprising:
determining a first temperature change rate specified for the first operational state of the first IT component; and
adjusting the temperature set point in increments that do not exceed the first temperature change rate, based on closed loop feedback of the interior air temperature value;
determining whether a temperature of the supply air provided to the first IT component is within the first temperature range; and
in response to determining that the temperature of the supply air is within the first temperature range, triggering activation of the first IT component into the first operating state following a hold time during which the first IT component is provided sufficient exposure to the supply air at the temperature set point.

2. The method of claim 1, further comprising:
monitoring one or more sensors that detect an interior humidity value;
determining a first humidity range specified for the first IT component that is scheduled to transition into the first operational state;
adjusting a humidity set point of the supply air provided to the first IT component to be within the first humidity range;
determining whether the interior humidity is within the first humidity range; and
triggering the activation of the first IT component to the first operational state further in response to determining that the interior humidity value is within the first humidity range, while an interior air temperature is within the first temperature range.

3. The method of claim 1, further comprising:
determining the hold time that provides sufficient exposure of the first IT component to the supply air at the temperature set point for a thermal mass of the first IT component to have an internal component temperature that is within the first temperature range; and
in response to determining that the interior component temperature is within the first temperature range, delaying, for a length of the hold time, the activation of the first IT component to the first operational state.

4. The method of claim 1, wherein the first operational state is a startup state, the method further comprising:
determining a second temperature range specified for the first IT component to function in a second operational state comprising an operating state;
adjusting the temperature set point of the management system to be within the second temperature range;
determining whether the temperature of the supply air provided to the first IT component is within the second temperature range; and
in response to determining that an interior air temperature is within the second temperature range, triggering the activation of the first IT component to the second operational state.

5. The method of claim 4, further comprising:
receiving a request to activate a second IT component of the more than one IT component;
determining a third temperature range specified in the specification data structure for the second IT component that is scheduled to transition into an operational state;
adjusting the temperature set point of the management system to be within an overlapping range of the second temperature range and the third temperature range;
determining whether the temperature of the supply air provided to the first IT component is within the third temperature range; and in response to determining that the temperature of the supply air is within the third temperature range, activating the second IT component to the operational state.

6. A management system that controls interior environmental conditions to facilitate operating state changes of more than one information technology (IT) component in a data center, the management system comprising:
    an environmental subsystem that provides supply air to moderate or cool a temperature of more than one IT component within the data center;
    one or more sensors that detect an interior air temperature value of the data center;
    a memory containing a cooling mode and equipment operating state (CM/EOS) application and a specification data structure containing environmental conditions specified to enable each one of the more than one IT component to function in one or more operational states; and
    a controller that is communicatively coupled to the environmental subsystem, the one or more sensors, and the memory, the controller executing the CM/EOS application to enable the management system to:
        monitor the one or more sensors that detect the interior air temperature value;
        access the specification data structure;
        determine a first temperature range specified in the specification data structure for the first IT component that is scheduled to transition into the first operational state;
        adjust a temperature set point of supply air provided by the environmental subsystem to the first IT component to be within the first temperature range, wherein the controller:
            determines a first temperature change rate specified for the first operational state of the first IT component and
            adjusts the temperature set point in increments that do not exceed the first temperature change rate, based on closed loop feedback of the interior air temperature value;
        determine whether a temperature of the supply air provided to the first IT component is within the first temperature range; and
        in response to determining that the temperature of the supply air is within the first temperature range, activate the first IT component to the first operational state following a hold time during which the first IT component is provided sufficient exposure to the supply air at the temperature set point.

7. The management system of claim 6, further comprising:
    one or more humidity sensors that detect an interior humidity value of the data center; and
    wherein the controller executes the CM/EOS application to enable the management system to:
        monitor the one or more sensors that detect the interior humidity value;
        determine a first humidity range specified in the specification data structure for the first IT component that is scheduled to transition into the first operational state;
        adjust a humidity set point of the supply air provided by the environmental subsystem to the first IT component to be within the first humidity range;
        determine whether the interior humidity is within the first humidity range; and
        trigger the activation of the first IT component to the first operational state further in response to determining that the interior humidity value is within the first humidity range, while an interior air temperature is within the first temperature range.

8. The management system of claim 6, wherein the controller executes the CM/EOS application to enable the management system to:
    determine a hold time that provides sufficient exposure of the first IT component to the supply air at the temperature set point for a thermal mass of the first IT component to have an internal component temperature that is within the first temperature range; and
    in response to determining that the internal component temperature is within the first temperature range, delay, for a length of the hold time, the activation of the first IT component to the first operational state.

9. The management system of claim 6, wherein:
    the first operational state is a startup state; and
    the controller executes the CM/EOS application to enable the management system to:
        determine a second temperature range specified in the specification data structure for the first IT component that is scheduled to transition into a second operational state comprising an operating state;
        adjust the temperature set point of the management system to be within the second temperature range;
        determine whether the temperature of the supply air provided to the first IT component is within the second temperature range based on the interior air temperature value; and
        in response to determining that the temperature of the supply air is within the second temperature range, activate the first IT component to the second operational state.

10. The management system of claim 9, wherein the controller executes the CM/EOS application to enable the management system to:
    receive a request to activate a second IT component of the more than one IT component;
    determine a third temperature range specified in the specification data structure for the second IT component that is scheduled to transition into an operational state;
    adjust the temperature set point of the management system that is within an overlapping range of the second temperature range and the third temperature range;
    determine whether the temperature of the supply air provided to the second IT component is within the third temperature range based on the interior air temperature value; and
    in response to determining that the interior air temperature value is within the third temperature range, activate the second IT component to the operational state.

11. A data center that controls interior environmental conditions to facilitate operating state changes of information technology (IT) components, the data center comprising:
    an enclosing structure;
    more than one heat-generating IT component positioned in the enclosing structure;
    environmental subsystem that provide supply air to moderate or cool a temperature of the more than one IT component within the data center;
    one or more sensors that detect an interior air temperature value of the data center;

a management system of the data center, the management system comprising:
- a memory containing a cooling mode and equipment operating state (CM/EOS) application and a specification data structure containing environmental conditions specified to enable each one of the more than one IT component to function in one or more operational states; and
- a controller that is communicatively coupled to the environmental subsystem, the one or more sensors, and the memory, the controller executing the CM/EOS application to enable the management system to:
  - monitor the one or more sensors that detect an interior air temperature value;
  - access the specification data structure;
  - determine a first temperature range specified in the specification data structure for the first IT component that is scheduled to transition into the first operational state;
  - adjust a temperature set point of supply air provided by the environmental subsystem to the first IT component to be within the first temperature range, wherein the controller:
    - determines a first temperature change rate specified for the first operational state of the first IT component; and
    - adjusts the temperature set point in increments that do not exceed the first temperature change rate, based on closed loop feedback of the interior air temperature value;
  - determine whether a temperature of the supply air provided to the first IT component is within the first temperature range; and
  - in response to determining that the temperature of the supply air is within the first temperature range, activate the first IT component to the first operational state following a hold time during which the first IT component is provided sufficient exposure to the supply air at the temperature set point.

12. The data center of claim 11, wherein:
the management system comprises one or more humidity sensors that detect an interior humidity value of the data center; and
the controller executes the CM/EOS application to enable the management system to:
- monitor the one or more sensors that detect the interior humidity value;
- determine a first humidity range specified in the specification data structure for the first IT component that is scheduled to transition into the first operational state;
- adjust a humidity set point of the supply air provided by the environmental subsystem to cause the first IT component to be within the first humidity range;
- determine whether the interior humidity is at/within the first humidity range; and
- trigger the activation of the first IT component to the first operational state further in response to determining that the interior humidity is within the first humidity range, while an interior air temperature is within the first temperature range.

13. The data center of claim 11, wherein the controller executes the CM/EOS application to enable the management system to:
- determine a hold time that provides sufficient exposure of the first IT component to the supply air at the temperature set point for a thermal mass of the first IT component to have an internal component temperature that is within the first temperature range; and
- in response to determining that an interior air temperature is within the first temperature range, delay, for a length of the hold time, the activation of the first IT component to the first operational state.

14. The data center of claim 11, wherein:
the first operational state is a startup state; and
the controller executes the CM/EOS application to enable the management system to:
- determine a second temperature range specified in the specification data structure for the first IT component that is scheduled to transition into a second operational state comprising an operating state;
- adjust the temperature set point of the management system to be within the second temperature range;
- determine whether the temperature of the supply air provided to the first IT component is within the second temperature range based on the interior air temperature value; and
- in response to determining that an interior air temperature is within the second temperature range, activate the first IT component to the second operational state.

15. The data center of claim 14, further comprising a second IT component of the more than one IT component, wherein the controller executes the CM/EOS application to enable the management system to:
- receive a request to activate a second IT component of the more than one IT component;
- determine a third temperature range specified in the specification data structure for the second IT component that is scheduled to transition into an operational state;
- adjust the temperature set point of the management system that is within an overlapping range of the second temperature range and the third temperature range;
- determine whether the temperature of the supply air provided to the second IT component is within the third temperature range based on the interior air temperature value; and
- in response to determining that the temperature of the supply air is within the third temperature range, activate the second IT component to the operational state.

16. The data center of claim 11, wherein the enclosing structure comprises a volumetric container that is transportable to a deployed operating location of the data center.

* * * * *